US008919230B1

(12) United States Patent  
Gao (10) Patent No.: US 8,919,230 B1  
(45) Date of Patent: Dec. 30, 2014

(54) TORQUE-LIMITING DRIVER WITH A SELF-LOCKING ADAPTER

(76) Inventor: Hua Gao, Fox Point, WI (US)

(*) Notice: Subject to any disclaimer, the term of this patent is extended or adjusted under 35 U.S.C. 154(b) by 559 days.

(21) Appl. No.: 13/351,118

(22) Filed: Jan. 16, 2012

(51) Int. Cl.
    *B25B 23/14* (2006.01)

(52) U.S. Cl.
    USPC .............. 81/467; 81/177.2; 81/438; 279/30; 279/22; 279/906

(58) Field of Classification Search
    USPC .............. 81/467, 472–474, 177.2, 438, 59.1; 279/22, 75, 905, 906
    See application file for complete search history.

(56) References Cited

U.S. PATENT DOCUMENTS

| | | | |
|---|---|---|---|
| 1,307,937 A | 6/1919 | Straub | |
| 2,289,583 A | 7/1942 | Malone | |
| 3,398,965 A * | 8/1968 | Cox | 279/30 |
| 3,734,516 A * | 5/1973 | Smith | 279/75 |
| 5,741,263 A | 4/1998 | Umber et al. | |
| 5,928,241 A | 7/1999 | Menut et al. | |
| 6,179,302 B1 | 1/2001 | Gauthier et al. | |
| 7,086,313 B2 | 8/2006 | Cantlon | |
| 7,287,449 B2 * | 10/2007 | Abel et al. | 81/177.2 |
| 7,810,817 B1 | 10/2010 | Gao | |
| 8,764,025 B1 * | 7/2014 | Gao | 279/30 |

OTHER PUBLICATIONS

U.S. Appl. No. 13/229,454, Gao, Hua.

* cited by examiner

*Primary Examiner* — Monica Carter  
*Assistant Examiner* — Melanie Alexander  
(74) *Attorney, Agent, or Firm* — Absolute Technology Law Group, LLC (57) ABSTRACT

An internal adapter for use in torque-limiting handles for interchangeable orthopedic tools contains a slidable collar component, house component, retaining ring, spring, driver component, cover and cam which engages a torque-limiting mechanism. A plurality of securing ball mechanisms releasably secure an orthopedic tool in the adapter, while a configuration of chamfered surfaces centrally stabilize the tool. A plurality of guiding chamfers located in a driver component rotationally secures the orthopedic tool.

20 Claims, 12 Drawing Sheets

TORQUE-LIMITING DRIVER WITH A SELF-LOCKING ADAPTER

FIELD OF INVENTION

The present invention relates to the field of medical devices, and more specifically to a self-locking internal adapter for securing medical tools.

TERMS OF ART

As used herein, the term "adapter" refers to a component of an orthopedic tool handle which engages a tool, As used herein, the term "chamfer" refers to a beveled, angled or tapered edge which engages the edge of a second component to create a secured junction.

As used herein, the terms "flattened portion" or "partially flattened portion" refer to a cylindrical surface having an area with a curvature less than that of the cylindrical curvature. A flattened or partially flattened portion may contain a single area or multiple areas of lesser curvature.

As used herein, the term "securing ball" refers to any structure or combination of structures which may engage a securing ball detent aperture. A securing ball may be any shape, including, but not limited to, spherical, quasi-spherical, rounded, oblong, ellipsoidal, and combinations of these and other shapes capable of engaging a securing ball detent aperture.

BACKGROUND

Adjustment tools are used in orthopedic surgery to tighten and adjust mechanical components within orthopedic devices. For example, screwdrivers, spreaders, pliers, hammers, cutters and other tools may be used to adjust screws, pins, rods and other orthopedic devices. The adjustment tools for adjusting these orthopedic devices must be highly stable to allow for precise adjustments, and many types of adjustments may be needed.

In order to save space on an operating room instrument table or in a sterilization kit, different orthopedic tools may be designed to be interchangeable with a single handle. For example, it is known in the art to fashion tools of varying lengths with shafts that may be inserted into a single tool handle.

As a result, a typical orthopedic tool may actually be a system of three components: a handle, an adapter and a tool. Generally; the handle and the adapter are structurally integrated and permanently attached to each other. Tools are adapted for insertion into the adapter.

Adapters for securing medical tools, specifically medical tools with a square or hexagonal shaft, to handles are known in the art. Every adapter has some sort of channel or orifice to receive the tool, and a locking mechanism to secure the tool in place. The function and simplicity of operating the locking mechanism are critical. Even incremental improvements in a locking mechanism can be critical to the outcome of a surgery.

Tools must be compact to allow an orthopedic surgeon to perform adjustments to orthopedic devices and other tasks within the confined space of various body regions.

Tools must also be versatile, and it is desirable to have as many tools as possible adapted for use with a single adapter and handle.

Adapter components are likely to come in contact with bodily fluids and other contaminants during medical procedures. Any contours, grooves and other hard-to-reach surfaces need to be carefully cleaned and sterilized. Exposed attachment components are also more likely to be bumped or inappropriately forced in an attempt to attach a medical tool. As a result, exposed attachment components are frequently damaged.

It is desirable to have an adapter for securing medical tools to handles which reduce the number of exposed components and surfaces.

It is desirable to have an apparatus for securing and grasping tools which is as compact as possible so that surgeons can operate within the limited spaces and contours of various regions of the body.

It is critical to have an adapter for securing medical tools in place as effectively and simply as possible.

U.S. Pat. No. 7,343,824 discloses a torque-limiting driver for orthopedic tools having an internal cam and external tool adapter. It is desirable to provide an internal adapter for a torque-limiting driver handle with an internal cam.

SUMMARY OF THE INVENTION

The present invention is an internal adapter for use in torque-limiting handles for interchangeable orthopedic tools. An internal adapter contains a slidable collar component, house component, retaining ring, spring, driver component, cover and cam which engages a torque-limiting mechanism. A plurality of securing ball mechanisms releasably secure an orthopedic tool in the adapter, while a configuration of chamfered surfaces centrally stabilizes the tool. A plurality of guiding chamfers located in a driver component rotationally secures the orthopedic tool.

DETAILED DESCRIPTION OF INVENTION

For the purpose of promoting an understanding of the present invention, references are made in the text to exemplary embodiments of an internal adapter for a torque limiting driver for orthopedic tools, only some of which are described herein. It should be understood that no limitations on the scope of the invention are intended by describing these exemplary embodiments. One of ordinary skill in the art will readily appreciate that alternate but functionally equivalent structures and materials may be used. The inclusion of additional elements may be deemed readily apparent and obvious to one of ordinary skill in the art. Specific elements disclosed herein are not to be interpreted as limiting, but rather as a basis for the claims and as a representative basis for teaching one of ordinary skill in the art to employ the present invention.

It should be understood that the drawings are not necessarily to scale; instead, emphasis has been placed upon illustrating the principles of the invention. In addition, in the embodiments depicted herein, like reference numerals in the various drawings refer to identical or near identical structural elements.

Figure 1:
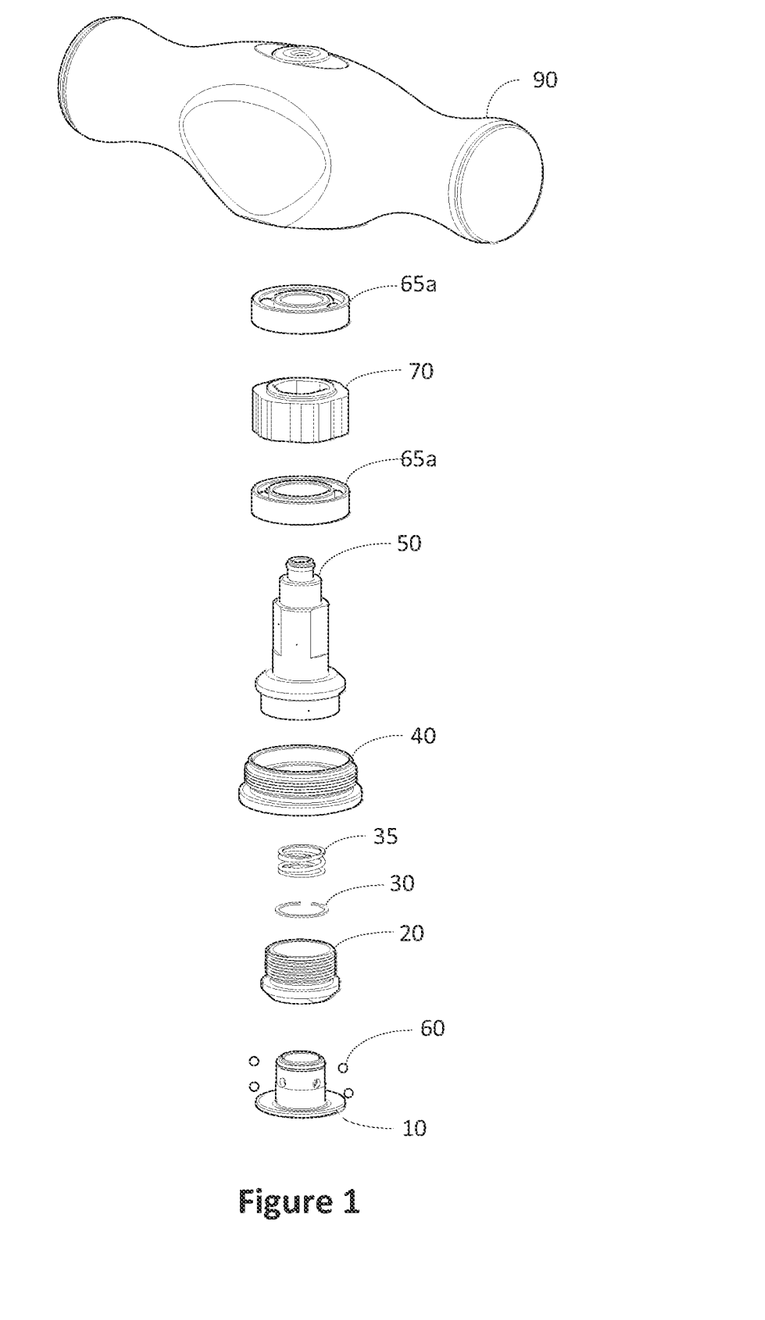
FIG. 1 is an exploded view of an exemplary embodiment of an internal adapter for a torque-limiting driver.

FIG. 1 is an exploded view of an exemplary self-locking internal adapter 100 for a torque limiting driver. Internal adapter 100 contains collar component 10, tapered housing 20, retaining ring 30, spring 35, cover 40, driver 50, bearings 65a, 65b and cam 70. Securing balls 60a, 60b, 60c, 60d are also shown. When assembled, internal adapter is configured to be secured and housed in torque-limiting driver 90.

As illustrated in FIG. 1, collar component 10, tapered housing 20, retaining ring 30, spring 35, cover 40, driver 50, bearings 65a, 65b and cam 70 are shown as separately manufactured components. In further exemplary embodiments, two or more of collar component 10, tapered housing 20, retaining ring 30, spring 35, cover 40, driver 50, bearings 65a, 65b and cam 70 may be integrally manufactured or machined. In still further exemplary embodiments, one or more of collar component 10, tapered housing 20, retaining ring 30, spring 35, cover 40, driver 50, bearings 65a, 65b and cam 70 may be integrally manufactured with torque-limiting driver 90.

As illustrated in FIG. 1, retaining ring 30 has gap 31. In further exemplary embodiments, retaining ring 30 may be a complete ring without gaps.

Bearings 65a, 65b are shown as standard ball bearings known in the art. In further exemplary embodiments, bearings 65a, 65b may be any bearings known in the art.

Figure 2:
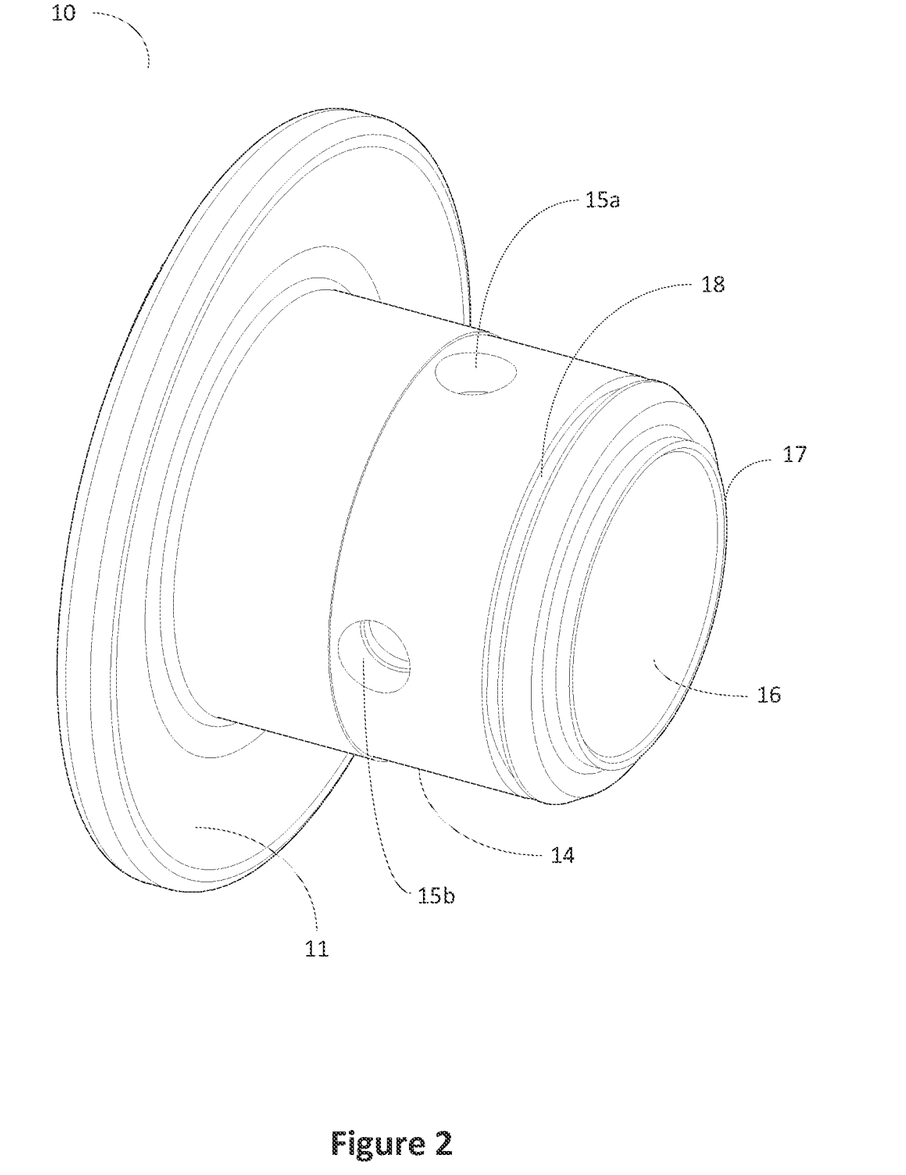
FIG. 2 illustrates an exemplary embodiment of a collar component for an internal adapter.

FIG. 2 illustrates an exemplary embodiment of collar component 10. Collar component 10 contains external collar base 11 and tubular sliding portion 14, with tool receiving channel 16 extending the length of collar component 10. In the exemplary embodiment shown, tubular sliding portion 14 contains securing ball apertures 15a, 15b (15c, 15d not shown). Securing ball apertures 15a, 15b, (15c, 15d not shown) are equidistant and symmetrically arranged around tubular sliding portion 14.

In further exemplary embodiments, tubular sliding portion 14 may contain additional securing ball apertures. While equidistant and symmetrically arranged securing ball apertures provides for greater securing and stability, in further exemplary embodiments, securing ball apertures may be asymmetrically arranged and positioned at varying distances around tubular sliding portion 14.

Securing ball apertures 15a, 15b, 15c, 15d contain a contoured inner surface which creates a diameter smaller than the diameter of securing balls 60a, 60b, 60c, 60d (not shown) at the innermost edge of securing ball apertures 15a, 15b, 15c, 15d. Securing balls 60a, 60b, 60c, 60d (not shown) are therefore freely rotatable within securing ball apertures 15a, 15b, 15c, 15d but may not pass through securing ball apertures 15a, 15b, 15c, 15d. In further exemplary embodiments, securing ball apertures 15a, 15b, 15c, 15d may contain a lip, rim, ridge or other structure which narrows the diameter of the innermost edge of securing ball apertures 15a, 15b, 15c, 15d to prevent securing balls 60a, 60b, 60c, 60d (not shown) from passing through.

FIG. 2 also shows tool receiving channel 16 extending the length of collar component 10. In the exemplary embodiment illustrated, tool receiving channel 16 is round tubular with a smooth surface and consistent internal diameter. In further exemplary embodiments, tool receiving channel may contain projections or grooves or may have an inconsistent internal diameter to accommodate a specifically manufactured tool.

The rear end of tubular sliding portion 14 contains protuberance 17 and groove 18, both of which span the external circumference of tubular sliding portion 14.

Figure 3:
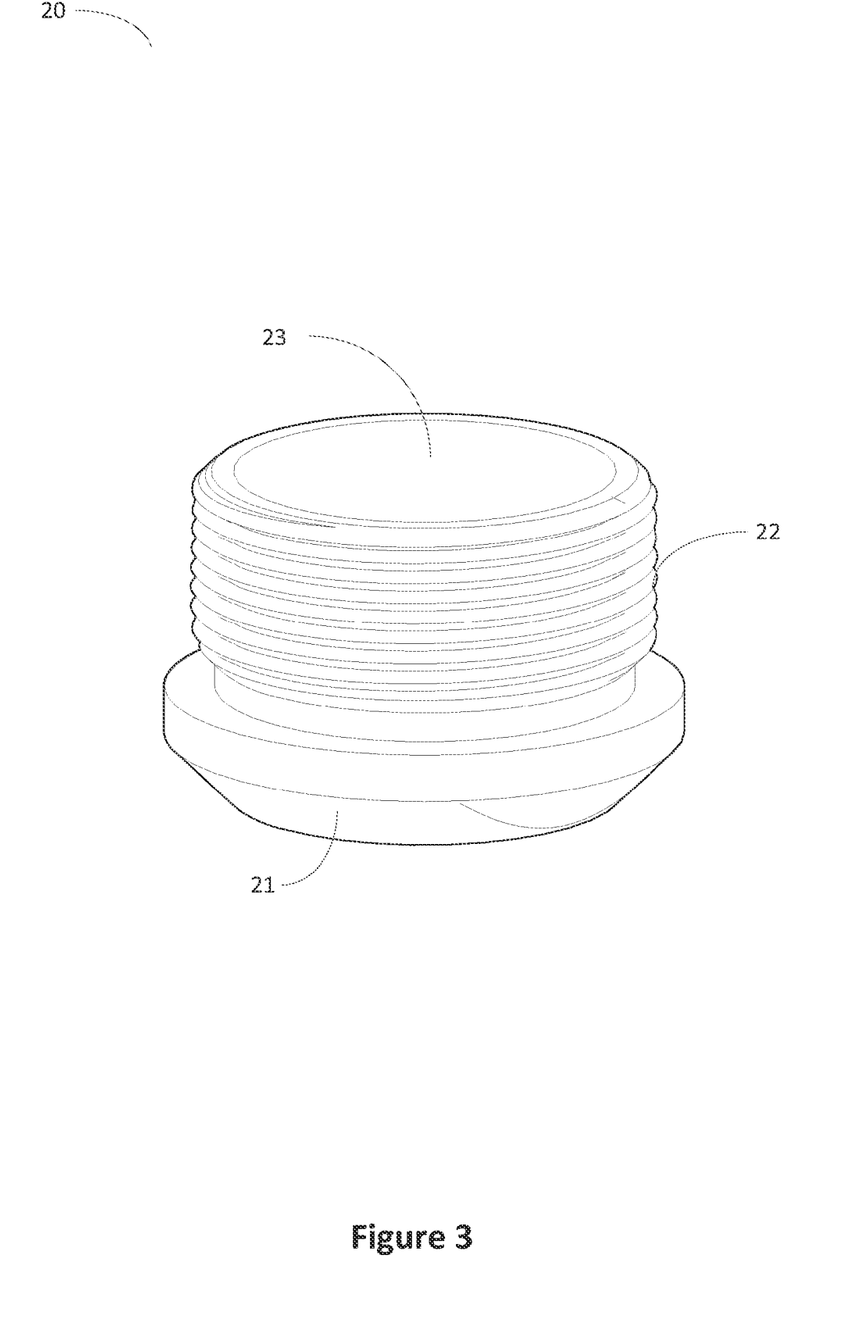
FIG. 3 illustrates an exemplary embodiment of a tapered housing for an internal adapter.

FIG. 3 is an exemplary embodiment of tapered housing 20. As shown in FIG. 3, tapered housing 20 contains external house base 21 with threaded driver-engaging stem 22. Interior collar channel 23 extends the length of tapered housing 20.

Figure 4:
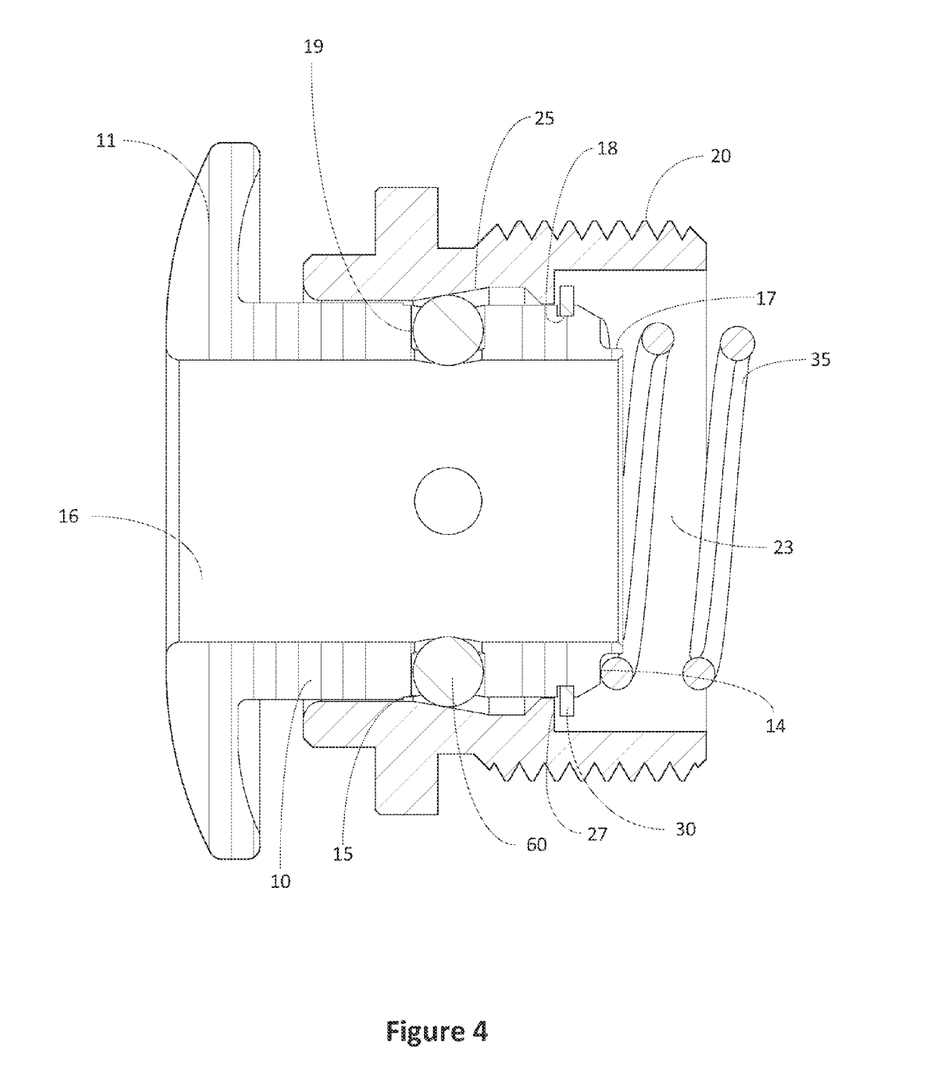
FIG. 4 is an exemplary self-locking mechanism for an internal adapter.

FIG. 4 illustrates collar component 10 joined with tapered housing 20b to create a self-locking mechanism. Collar component 10 is slidably engaged with the inner surface of interior collar channel 23.

Securing balls 60 each correspond with one of securing ball apertures 15. Securing ball apertures 15 have contoured inner surface 19, so that the inner diameter of securing ball apertures 15 is slightly less than that of securing balls 60, so that securing balls 60 do not fall through securing ball apertures 15 but remain freely rotatable in securing ball apertures 15. The interior surface of interior collar channel 23 creates a cover over securing ball apertures 15 to prevent securing balls 60 from disengaging securing ball apertures 15.

In other exemplary embodiments, securing ball apertures 15 may contain lips, ridges, protuberances, contours or other structures which create a smaller inner diameter and prevent securing balls 60 from falling through securing ball apertures 15.

Interior collar channel 23 also contains tapered surface 25. The inner diameter of interior collar channel 23 is smaller near the opening of interior collar channel 23 and progressively larger inward of the opening.

As spring 35 exerts outward force on collar component 10, securing balls 60 in securing ball apertures 15 are forced to align with the outer-most, or narrowest, part of tapered surface 25. Retaining ring 30, in groove 18, is also pushed against stop ridge 27 of tapered housing 20, which prevents collar component 10 from being forced too far outward by spring 35.

As an orthopedic tool would be pushed into tool receiving channel 16, securing balls 60 freely rotate within securing ball apertures 15, allowing the tool shaft to proceed through tool receiving channel 16. When a tool shaft is pushed into tool receiving channel 16, securing balls 60 are forced slightly towards the inner-most, or wider, part of tapered surface 25.

If the tool is pulled out from tool receiving channel 16, securing balls 60 are forced toward the outer-most, or narrowest, part of tapered portion 25, so that securing balls 60 are no longer able to freely rotate. The tool shaft is therefore locked within tool receiving channel 16.

To remove a tool from tool receiving channel 16, external collar base 11 is pressed inward. Spring 35 is compressed, and collar component 10 slides inward within interior collar channel 23. Securing ball apertures 15 align with the inner-most, or widest, part of tapered portion 25, which increases the volume of securing ball apertures 15. Securing balls 60 are then able to freely rotate within securing ball apertures 15, allowing the tool shaft to be pulled out of tool receiving channel 16.

Figure 5A:
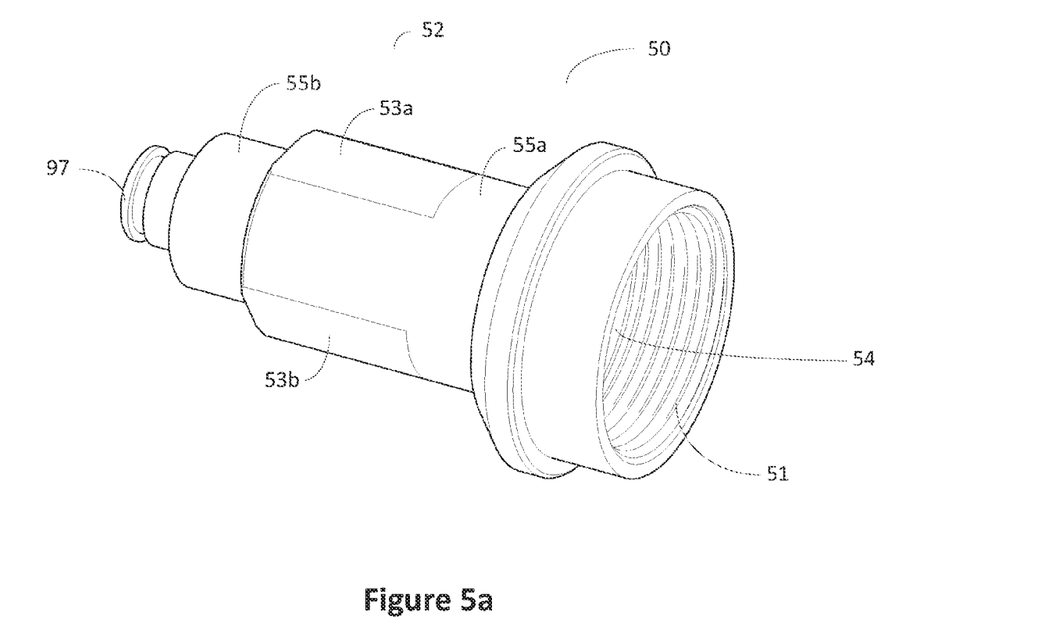
FIGS. 5a and 5b illustrate an exemplary embodiment of a driver for an internal adapter.
Figure 5B:
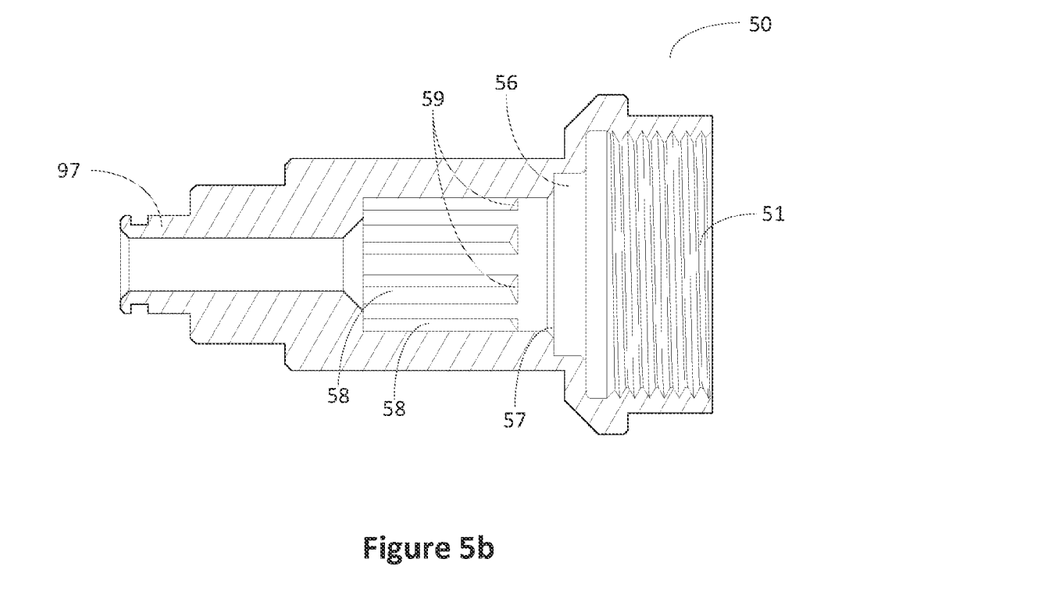

FIGS. 5a and 5b illustrate an exemplary driver 50. Driver 50 has front threaded portion 51 which corresponds with threaded driver-engaging stem 22 (not shown) of tapered housing 20 (not shown). Tool guiding channel 54 extends the length of driver 50. Handle-engaging projection 97 projects from the rear of driver 50.

Driver 50 also has bearing shaft surfaces 55a, 55b, which correspond to bearings 65a, 65b, (not shown) respectively, and three flattened surfaces 53a, 53b, 53c (not shown), between bearing shaft surfaces 55a, 55b, which correspond to the inner flattened surfaces of cam 70 (not shown).

In the exemplary embodiment shown, tapered rear portion contains two bearing shaft surfaces 55a, 55b and three flattened surfaces 53a, 53b, 53c (not shown). In further exemplary embodiments, tapered rear portion may contain additional bearing shaft surfaces to correspond to the number of bearings being used. Tapered rear portion may also contain a different number of flattened surfaces in order securely engage a cam being used.

Internally, driver 50 contains spring house 56, which secures spring 35 (not shown) between driver 50 and collar component 10 (not shown). Leading chamfer 57 transitions tool guiding channel 54 to a smaller internal diameter with guiding chamfers 58. In the exemplary embodiment shown, tool guiding channel 54 contains eight double square guiding chamfers 58. In further exemplary embodiments, guiding chamfers may be hexagonal or other configuration, and tool guiding channel 54 may contain more or fewer guiding chamfers 58 to correspond to a specific tool shaft or other guiding chamfer configuration.

As illustrated in FIG. 5b, guiding chamfers 58 do not start at the edge of leading chamfer 57 and contain transition chamfer 59. As will be illustrated in FIGS. 8a, 8b and 8c, the proportional distance of transition chamfer 59 of guiding chamfers 58 from leading chamfer 57 is a critical dimension.

Figure 6A:
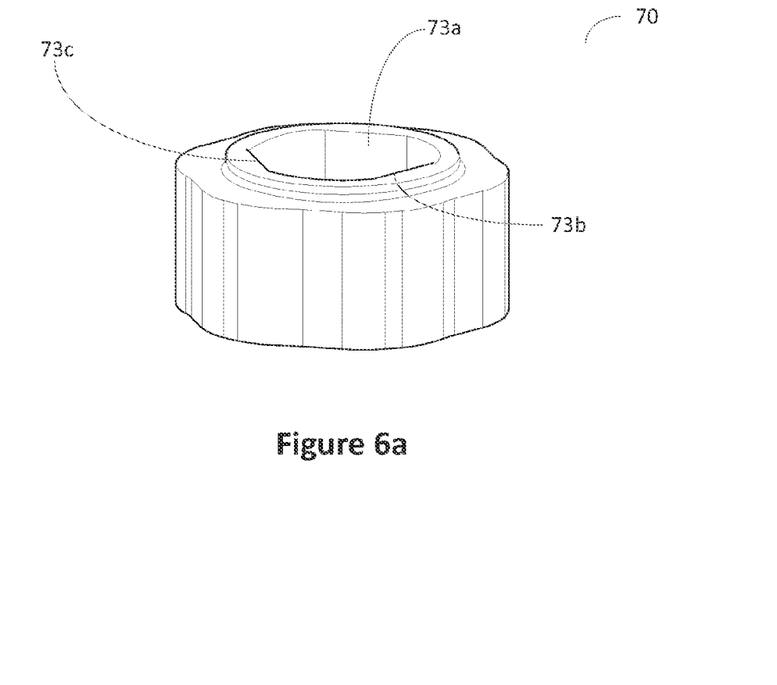
FIGS. 6a and 6b illustrate an exemplary cam for an internal adapter.
Figure 6B:
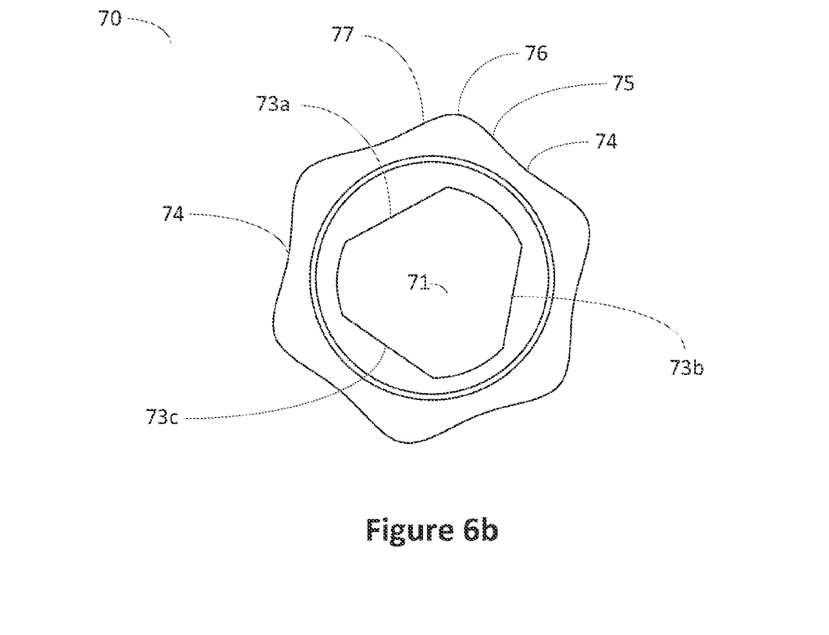

FIGS. 6a and 6b illustrate an exemplary embodiment of cam 70. As illustrated, cam 70 contains driver channel 71 which extends the length of cam 70. Driver channel 71 contains flattened surfaces 73a, 73b, 73c which correspond to flattened surfaces 53a, 53b, 53c (not shown) of driver 50 (not shown). When engaged, flattened surfaces 73a, 73b, 73c and 53a, 53b, 53c (not shown) prohibit rotation of driver 50 (not shown) within cam 70.

Cam 70 also contains external contours with a plurality of inclined areas 74 interposed between gradual sloped areas 75 and 77 that culminate in elevated areas 76. As will be illustrated in FIGS. 9, 10 and 11, roller 201 (not shown) of torque limiting mechanism 200 (not shown) will roll slowly up and down surfaces 75 and 77 when a maximum torque or pressure omit is reached.

In the exemplary embodiment shown, cam 70 contains six elevated areas 76 with six inclined areas 74. In further exemplary embodiments, cam 70 may contain any number of contours, and contours may be more or less rounded depending on the roller or torque assembly being used.

Figure 7:
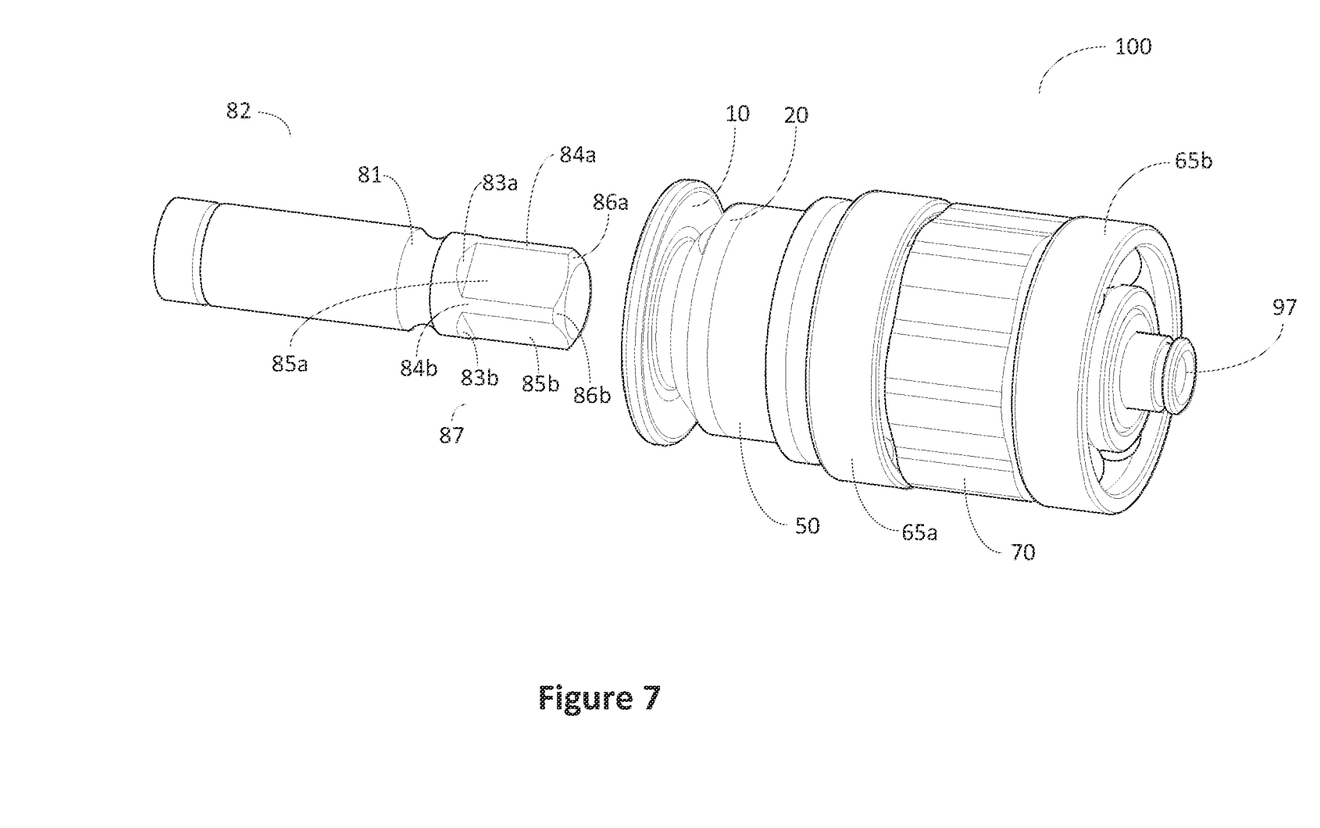
FIG. 7 illustrates an exemplary internal adapter for a torque-limiting driver.

FIG. 7 is an exemplary embodiment of assembled internal adapter 100 without cover 40 (not shown) for use with tool shaft 82. Bearings 65a, 65b and cam 70 are secured around driver 50, with rear portion 97 of driver 50 protruding from bearing 65b. Driver 50 secures collar component 10 and tapered housing 20.

At one end of tool shaft 82 is handle-engaging portion 87. The opposite end of tool shaft 82 may contain any tool known in the art.

As illustrated in FIG. 7, groove 81 transitions tool shaft 82 to handle-engaging portion 87, which is squared with flat surfaces 85a, 85b (85c, 85d not shown). In further exemplary embodiments, handle-engaging portion 87 may be hexagonal or any other configuration known in the art.

Flat surfaces 85a, 85b (85c, 85d not shown) each have a corresponding chamfer 83a (83b, 83c, 83d not shown) and are separated by rounded transitions 84a, 84b (84c, 84d not shown), each also having a corresponding chamfer 86a, 86b (86c, 86d not shown). The distance from the center of groove 81 to the edge of chamfer 86a (labeled as A in FIGS. 8a, 8b and 8c) is a critical distance, as will be shown in FIGS. 8a, 8b and 8c.

Figure 8A:
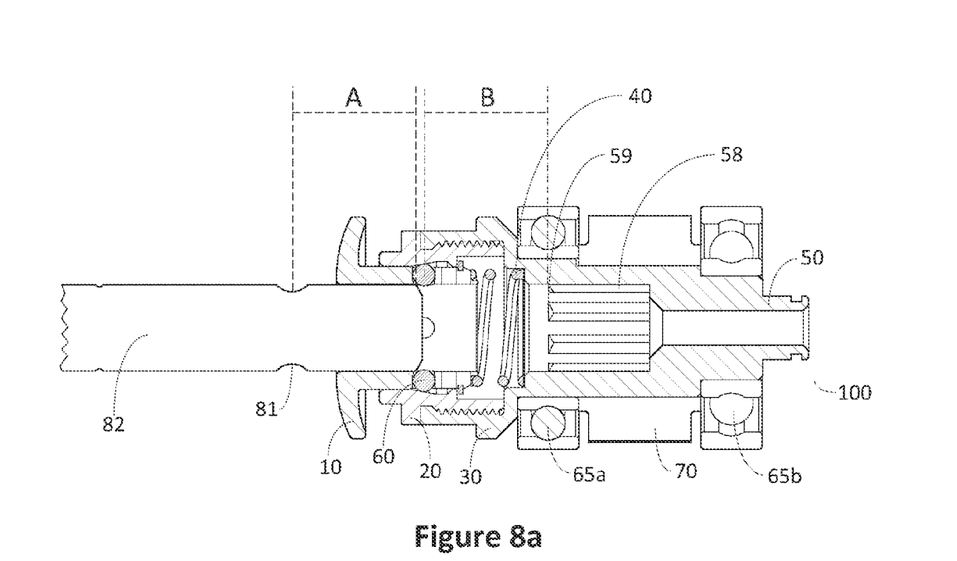
FIGS. 8a, 8b and 8c illustrate an exemplary internal adapter engaging a tool shaft.
Figure 8B:
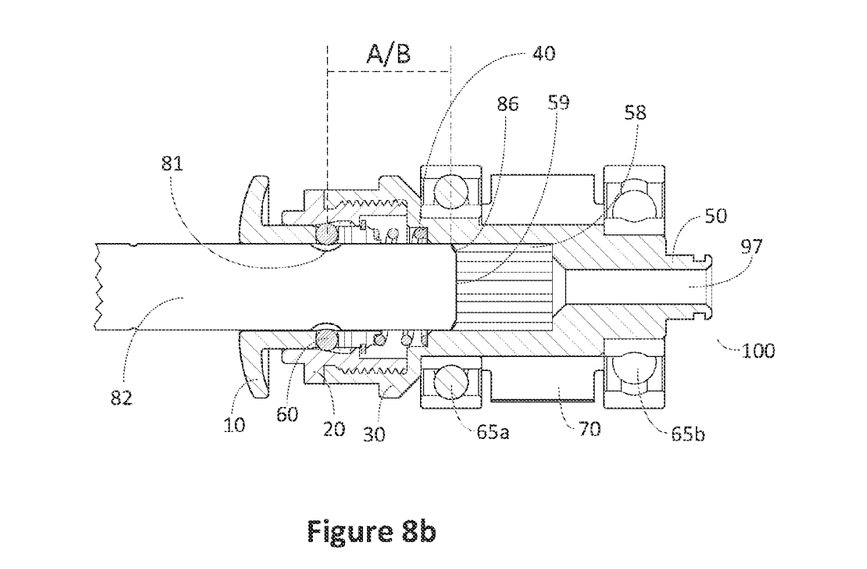
Figure 8C:
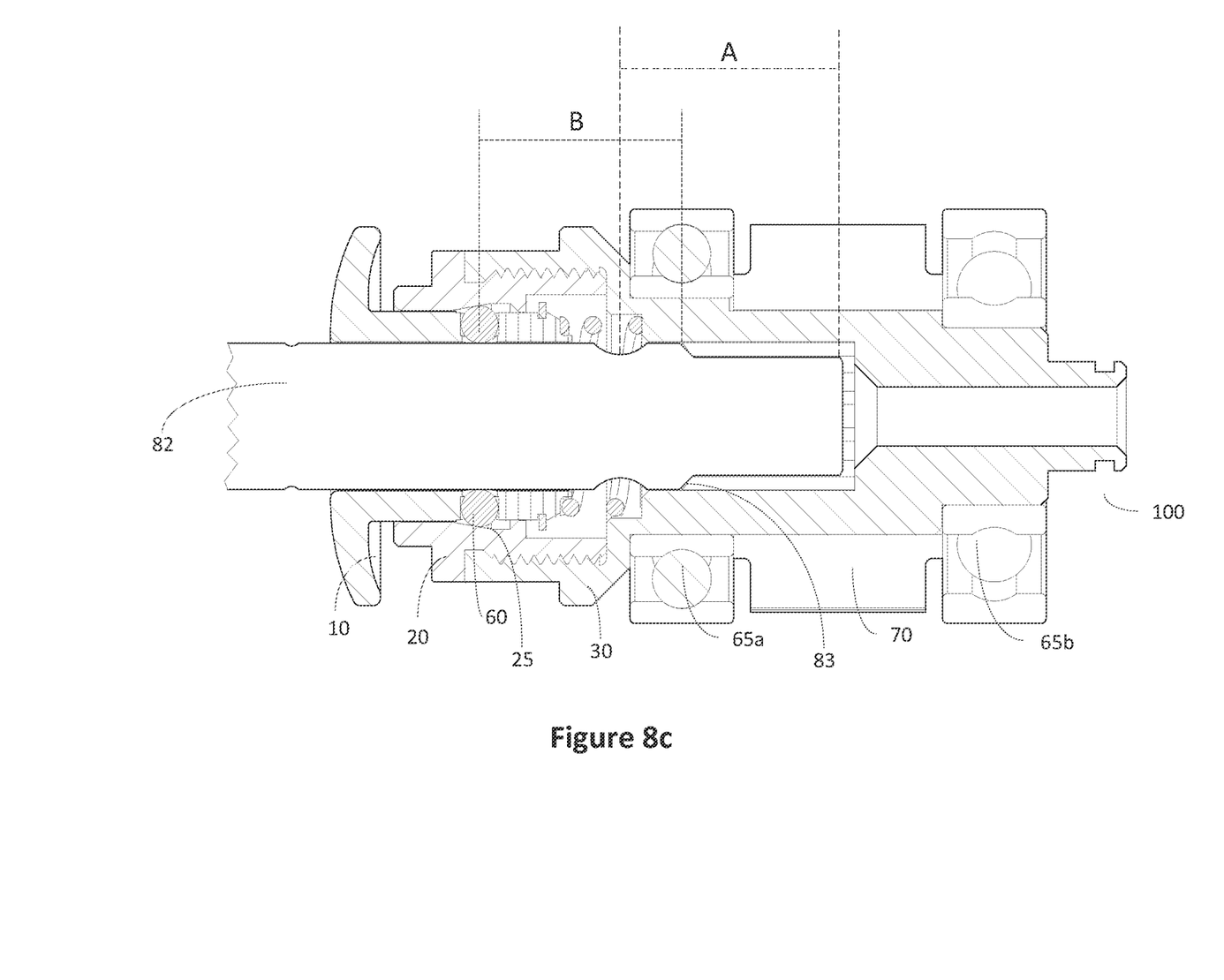

FIGS. 8a, 8b and 8c illustrate an exemplary embodiment of internal adapter 100 engaging tool shaft 82.

As illustrated in FIG. 8a, tool shaft 82 is partially inserted into internal adapter 100. Chamfers 86 engage securing balls 60 and force them into the larger area created by tapered portion 25. Securing balls 60 are able to freely rotate in securing ball apertures 15 (not shown) and tool shaft 82 is able to pass through tool receiving channel 16 (not shown). The distance from the center of securing balls 60 to leading transition chamfer 59 of guiding chamfers 58 is labeled as B.

In the exemplary embodiment shown, distance A is equal to distance B. It is critical that distances A and B are equal to provide quick and secure locking of tool shaft 82 in internal adapter 100.

In FIG. 8b, tool shaft 82 is further in tool receiving channel 16 (not shown), with groove 81 aligned with securing balls 60 and chamfers 86 aligned with leading transition chamfer 59 of guiding chamfers 58. In order to fully secure tool shaft 82 in internal adapter 100, flat surfaces 85 (not shown) must properly align with guiding chamfers 58. Securing balls 60 do not engage tool shaft 82 in this position, allowing tool shaft 82 to freely rotate within tool receiving channel 16 and be properly oriented to engage guiding chamfers 58.

FIG. 8c illustrates tool shaft 82 secured within internal adapter 100. Tool shaft 82 is aligned so that handle-engaging portion 87 is aligned with guiding chamfers 58 (not shown) to prevent rotational movement of tool shaft 82 in driver 50. Securing balls 60 are positioned along the portion of tapered surface 25 of tapered housing 20 creating a smaller volume for securing ball apertures 15 (not shown) and engage tool shaft 82 to prevent movement of tool shaft 82 out of handle 90 (not shown).

If tool shaft 82 is pulled outward from handle 90 (not shown), securing balls 60 are unable to rotate within securing ball apertures 15 (not shown) and prevent movement of tool shaft 82. To release tool shaft 82, collar component 10 is pushed inward toward handle 90 (not shown) to compress spring 35. Securing balls 60 are aligned with the portion of tapered surface 25 creating a larger volume for securing ball apertures 15 (not shown). Securing balls 60 are therefore able to freely rotate in securing ball apertures 15 (not shown), allowing tool shaft 82 to be removed from internal adapter 100.

In the exemplary embodiment shown in FIG. 8c, chamfers 83 corresponding with flattened surfaces 85 (not shown) correspond to and engage leading transition chamfers 59 (not shown) to stabilize tool shaft 82 centrally in driver 50.

Figure 9:
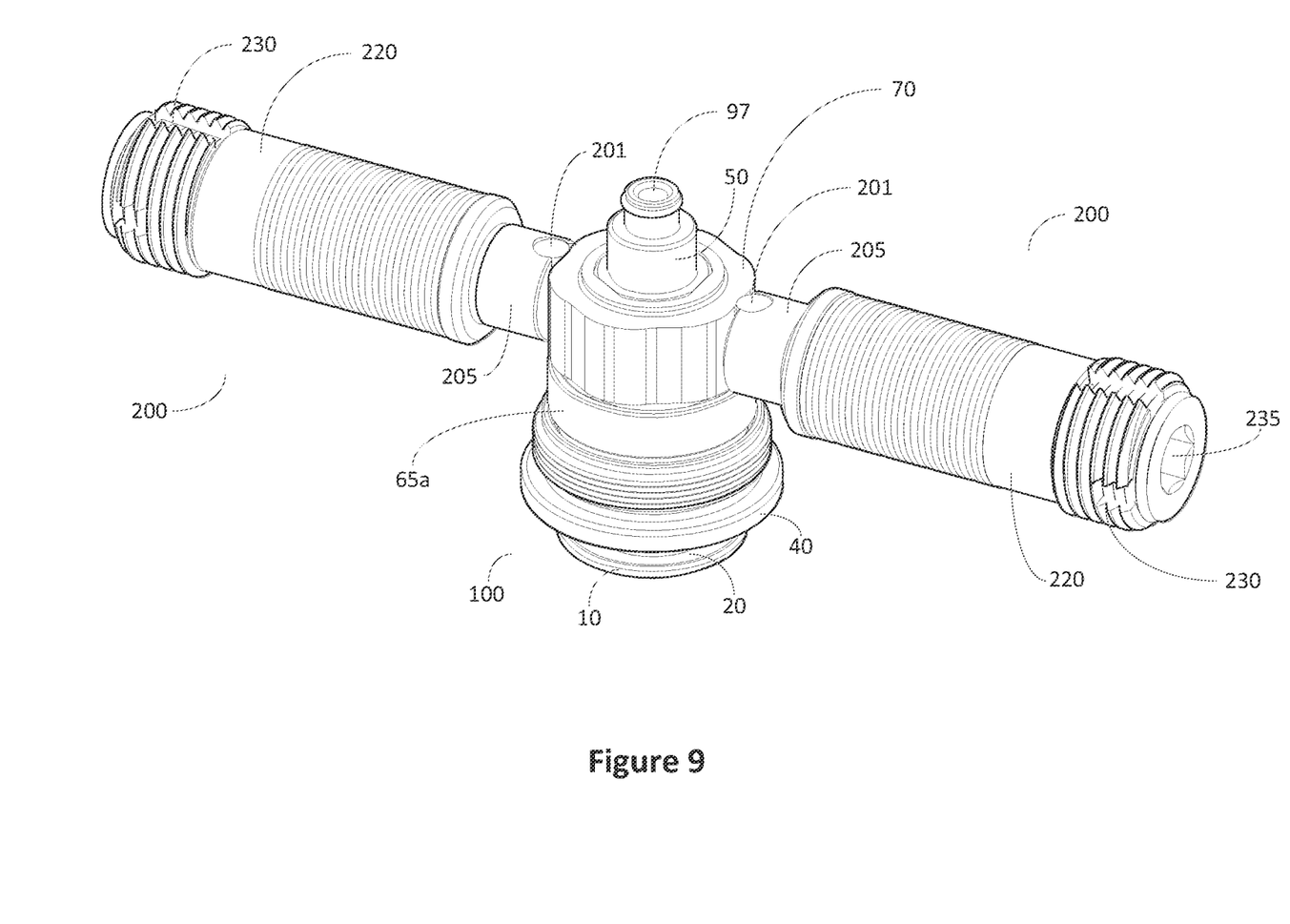
FIG. 9 illustrates an exemplary internal adapter assembled with a torque-limiting mechanism.
Figure 10:
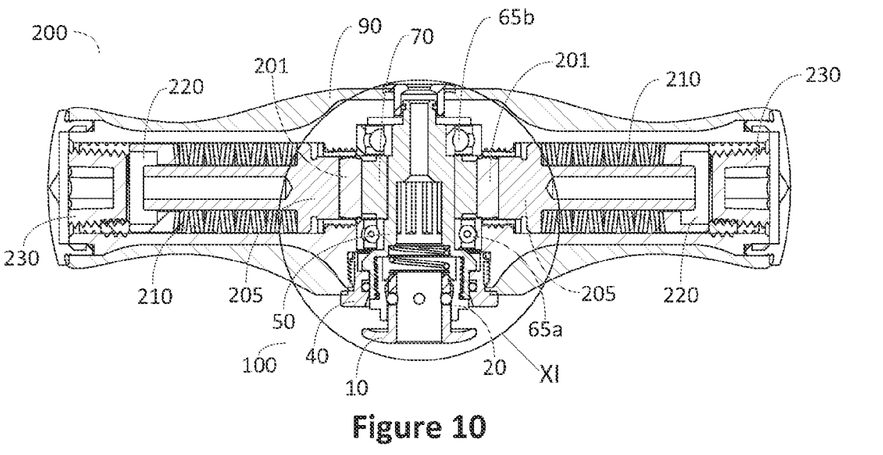
FIG. 10 illustrates an exemplary internal adapter with torque-limiting mechanism assembled inside a handle.

FIGS. 9 and 10 illustrate an exemplary internal adapter 100 fully assembled and connected with torque-limiting mechanism 200. In the exemplary embodiment shown in FIG. 9, torque-limiting mechanism is a torque-limiting mechanism as known in the art and includes spacers 220, locking screws 230 with plug screw 235, springs 210, plungers 205 and rollers 201 with rollers 201 adapted to engage cam 70. Cam 70 is secured on driver 50 with bearing 65a visible and bearing 65b (not shown) removed. In further exemplary embodiments, torque-limiting mechanism 200 may be any torque limiting mechanism known in the art, containing similar or equivalent components, and which provides a structural component adapted to engage cam 70.

As illustrated in FIG. 10, internal adapter 100, when secured in a handle, is stable between the rollers 201. Cover 40 secures internal adapter 100 to handle 90 and fits around assembled collar component 10, tapered housing 20 and driver 50.

Springs 210 exert pressure on plungers 205 to keep rollers 201 in physical engagement with cam 70 while a tool is in use. Rollers 201 are able to rotate against cam 70, easily slide over inclined areas 74 (not shown), sloped areas 75 and 77 (not shown) and elevated areas 76 (not shown). Once the desired torque is reached, springs 210 release pressure, causing a gap between rollers 201 and cam 70.

Both torque limiting mechanism 200 and internal adapter 100 are contained within handle cavity 92 (not shown) of handle 90, which in the exemplary embodiment shown has a T-shape. As illustrated, torque limiting mechanism 200 includes spacer 220, locking screw 230, spring 210, plunger 205 and roller 201, with roller 201 adapted to engage cam 70. In further exemplary embodiments, torque limiting mechanism 200 may be any torque limiting mechanism known in the art which provides a structural component adapted to engage cam 70.

Figure 11:
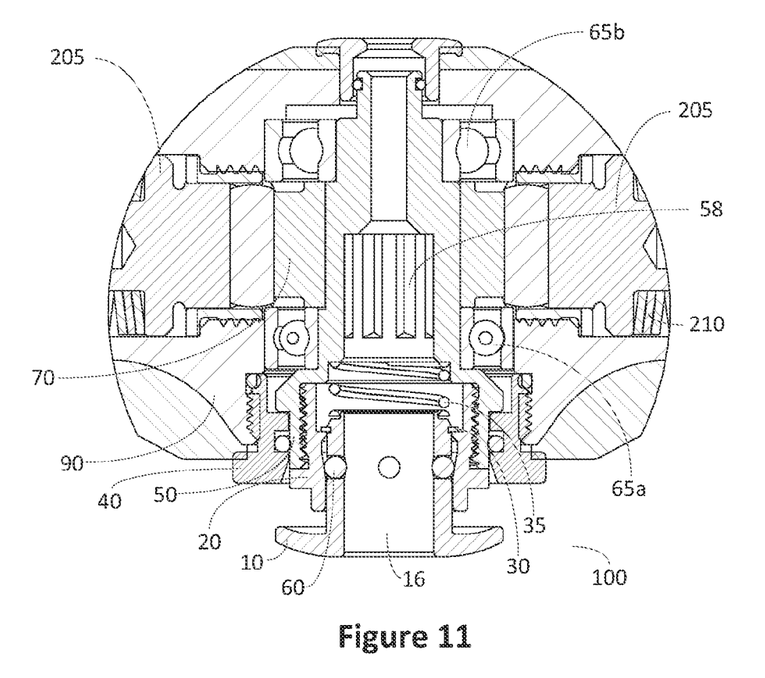
FIG. 11 illustrates a torque-limiting mechanism engaging an exemplary internal adapter.

FIG. 11 more closely shows the interaction of internal adapter 100 and torque limiting mechanism 200. Driver 50 is secured to tapered housing 20, with collar component 10 and securing balls 60 secured in interior collar channel 23 (not shown) by retaining ring 30 and forced outward by spring 35. Bearings 65a, 65b and cam 70 are around driver 50, with flattened surfaces 53a, 53b, 53c (not shown) of driver 50 engaging flattened surfaces 73a, 73b, 73c (not shown) of cam 70. Driver 50 is therefore unable to rotate within cam 70.

Cover 40 is shown secured to handle 90, thereby securing internal adapter 100 to handle 90. Torque-limiting mechanism 200 is also secured to handle 90.

When a tool is inserted in internal adapter 100, flat surfaces on the tool engage guiding chamfers 58, which center and stabilize the tool and prevent rotational movement of the tool within tool receiving channel 16. Similarly, the flattened surfaces on driver 50 engage the inner flattened surfaces of cam 70 to prevent rotational movement of driver 50, and therefore the tool, within cam 70.

When turning handle 90, springs 210 of torque limiting mechanism 200 exert force on plungers 205 and push rollers 201 in physical contact with cam 70. Cam 70 is therefore moved with handle 90 as handle 90 is rotated. Rotation of handle 90 and cam 70 causes driver 50 and ultimately the tool to rotate. Once the desired torque is reached, springs 210 no longer push on plungers 205, causing rollers 201 to lose physical contact with cam 70. As handle 90 is rotated, rollers 201 glide across the surface of cam 70, while cam 70 remains stationary. Handle 90 is therefore rotated while cam 70, driver 50, and, ultimately; the tool, remain stationary. Bearings 65a, 65b aid handle 90 is smoothly rotating about driver 50 when rollers 201 are not engaged with cam 70.

Figure 12:
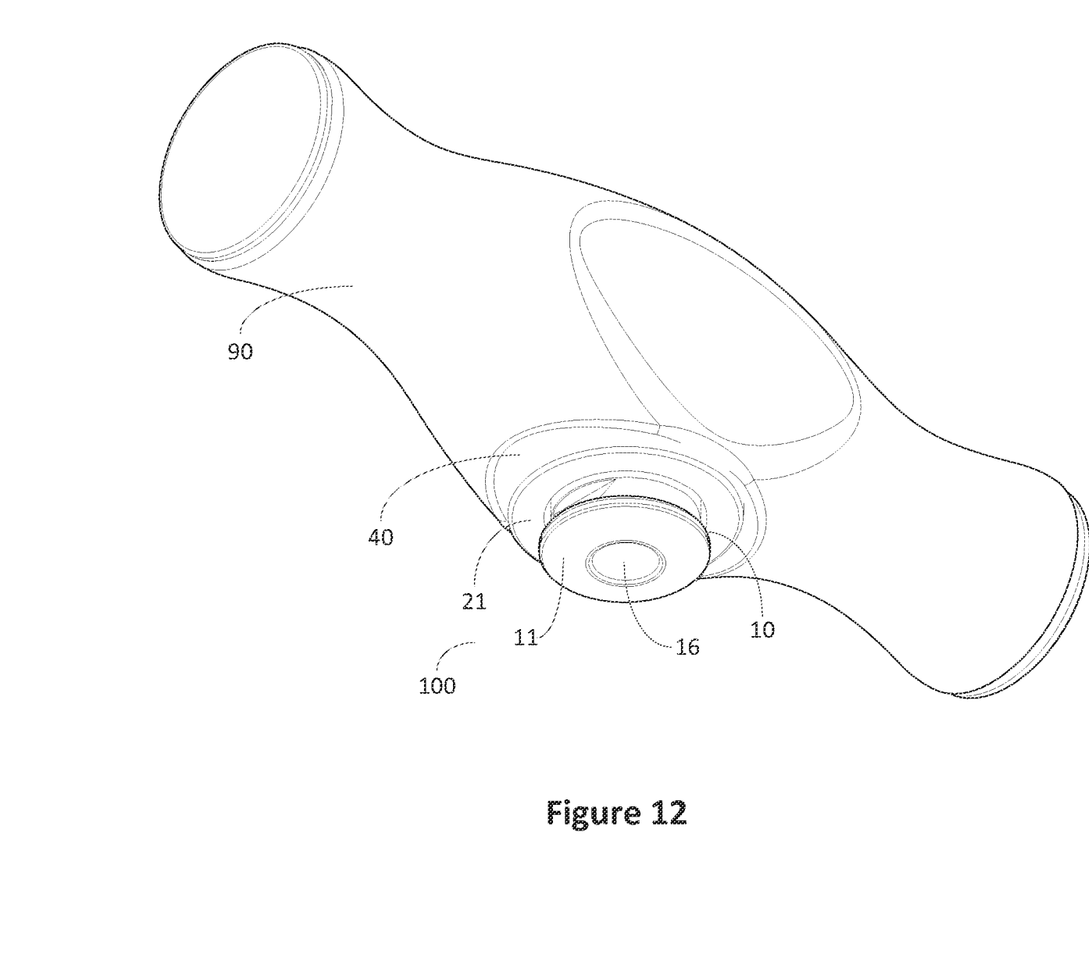
FIG. 12 is an exterior view of an exemplary internal adapter with torque-limiting mechanism assembled inside a handle.

FIG. 12 is an external view of internal adapter 100 assembled in handle 90 with torque limiting mechanism 200 (not shown). As illustrated, external collar base 11, external house base 21 and the outer-most surface of cover 40 are the only components of internal adapter 100 visible outside handle 90. In further exemplary embodiments, cover 40 may be entirely contained within handle 90. In still further exemplary embodiments, house 20 may be more recessed within handle 90, with external collar base 11 the only protruding portion of internal adapter 100. In still further embodiments, internal adapter 100 may be entirely encased by handle 90.

What is claimed is:

1. A torque-limiting tool handle for releasably engaging orthopedic tools comprised of:
    a tool handle and having an internal handle cavity;
    a plurality of components adapted to fit within said internal handle cavity to releasably secure an orthopedic tool in a manner that is sufficiently stable for use during an orthopedic procedure, wherein said plurality of components include
    a slidable collar component having an external collar base with an tubular sliding portion containing a plurality of securing ball detent apertures and a retaining ring groove,
    said tubular sliding portion creating an internal tool receiving channel and insertable into an interior collar channel of a housing component,
    said interior collar channel of said housing component having a tapered inner surface which covers said plurality of securing ball detent apertures, wherein said tapered inner surfaces creates a smaller interior collar channel diameter at the front of said interior collar channel and a larger interior collar channel diameter at the rear end of said interior collar channel, and a stop-ridge, wherein said slidable collar component is slidable within said interior collar channel and said plurality of securing ball detent apertures are aligned with said tapered surface,
    a plurality of securing balls wherein each one of said plurality of securing balls engages one of said plurality of securing ball detent apertures to decrease the diameter of said internal tool receiving channel,
    a retaining ring contained in said retaining ring groove,
    a spring adapted to provide outward force on said slidable collar component so that said plurality of securing balls are aligned with said smaller interior collar channel diameter and said retaining ring engages stop-ridge to prevent outward movement of said slidable collar component,
    a driver component having a plurality of guiding chamfers, and
    a cover which engages said internal handle cavity,
    wherein inward force applied to said slidable collar component aligns said plurality of securing balls with said larger interior collar channel diameter to increase the diameter of said tool receiving channel; and
    a cam, wherein said cam is secured to said driver component.

2. The apparatus of claim 1 which has four securing balls and four securing ball apertures.

3. The apparatus of claim 1 wherein said guiding chamfers are double square.

4. The apparatus of claim 1 wherein said driver component has at least one flattened exterior surface and said cam has at least one corresponding flattened internal surface to prevent rotational movement of said driver in said cam.

5. The apparatus of claim 1 which further includes at least one bearing.

6. The apparatus of claim 1 wherein said cover and said internal handle cavity contain corresponding threaded portions.

7. A torque-limiting handle for releasably securing an orthopedic tool comprised of:
    a tool handle and having an internal handle cavity;

a torque-limiting assembly housed within said internal handle cavity, said torque-limiting assembly including at least one roller; and at least one internal adapter adapted to fit within said internal handle cavity and releasbly secure the shaft of an orthopedic tool comprised of a slidable collar component with an internal tool receiving channel, said collar component having a plurality of securing ball apertures and a retaining ring groove, a house component with an interior collar channel having a tapered surface creating a smaller interior collar channel diameter at the front of said interior collar channel and a larger interior collar channel diameter at the rear end of said interior collar channel and a stop-ridge, wherein said slidable collar component is slidable within said interior collar channel and said plurality of securing ball apertures are aligned with said tapered surface, a plurality of securing balls wherein each one of said plurality of securing balls engages one of said plurality of securing ball apertures to decrease the diameter of said internal tool receiving channel, a retaining ring contained in said retaining ring groove, a spring adapted to provide outward force on said slidable collar component so that said plurality of securing balls are aligned with said smaller interior collar channel diameter and said retaining ring engages stop-ridge to prevent outward movement of said slidable collar component, a driver component having a plurality of guiding chamfers each having a transition chamfer, wherein said driver component secures said spring against said slidable collar component, and a cover which engages said internal cavity, wherein inward force applied to said slidable collar component aligns said plurality of securing balls with said larger interior collar channel diameter to increase the diameter of said tool receiving channel;

a cam, and at least one bearing, wherein said roller engages said cam.

8. The handle of claim 7 wherein said cam has a plurality of inclined areas interposed between gradual sloped areas that culminate in elevated areas.

9. The handle of claim 8 wherein said roller is freely rotatable against said cam.

10. The handle of claim 7 wherein said securing ball apertures are symmetrically arranged.

11. The handle of claim 7 wherein said guiding chamfers are double square.

12. The handle of claim 7 wherein said driver component has at least one flattened exterior surface and said earn has at least one corresponding flattened internal surface to prevent rotational movement of said driver in said cam.

13. The handle of claim 7 wherein said cover and said internal cavity contain corresponding threaded portions.

14. The handle of claim 7 wherein said shaft has a groove and a plurality of flattened surfaces separated by rounded transitions having corresponding chamfers, wherein the distance from the center of said groove to the leading edge of said corresponding chamfers is equal to the distance from the center of one of said securing balls to the leading edge of one of said transitional chamfers.

15. A torque-limiting handle for a medical shaft comprised of:

a handle having an internal handle cavity, wherein said internal handle cavity has a threaded portion;

a torque-limiting assembly housed within said internal handle cavity, said torque-limiting assembly including at least one roller; and an internal adapter configured to receive an orthopedic tool having a shaft with a groove and a plurality of flattened surfaces having corresponding chamfers and separated by rounded transitions having corresponding chamfers, said internal adapter being configured to fit within said internal handle cavity and comprised of a slidable collar component with an internal tool receiving channel, said collar component having a plurality of symmetrically arranged securing ball apertures and a retaining ring groove, a house component with an interior collar channel having a tapered surface creating a smaller interior collar channel diameter at the front of said interior collar channel and a larger interior collar channel diameter at the rear end of said interior collar channel and a stop-ridge, wherein said slidable collar component is slidable within said interior collar channel and said plurality of securing ball apertures are aligned with said tapered surface, a plurality of securing balls wherein each one of said plurality of securing balls engages one of said plurality of securing ball apertures to decrease the diameter of said internal tool receiving channel, a retaining ring contained in said retaining ring groove, a spring adapted to provide outward force on said slidable collar component so that said plurality of securing balls are aligned with said smaller interior collar channel diameter and said retaining ring engages stop-ridge to prevent outward movement of said slidable collar component, a driver component having a plurality of guiding chamfers corresponding to said flattened surfaces of said orthopedic tool and at least one flattened exterior surface, wherein said guiding chamfers have transition chamfers, and a handle-engaging cover having a threaded portion corresponding with said threaded portion of said internal cavity, wherein inward force applied to said slidable collar component aligns said plurality of securing balls with said larger interior collar channel diameter to increase the diameter of said tool receiving channel; and a cam having an interior channel with at least one flattened surface; wherein said roller engages said cam;

wherein said at least one flattened exterior surface of said driver and said at least one flattened surface of said cam interior channel correspond to prevent rotational movement of said driver in said cam;

wherein the distance from the center of said groove to the leading edge of said chamfers corresponding to said rounded transitions of said tool shaft is equal to the distance from the center of one of said securing balls to the leading edge of one of said transition chamfers of said driver component and wherein said slidable collar component, said house component, said securing balls, said retaining ring, said spring, said driver component, said cover and said cam are housed within said housing.

16. The handle of claim 15 wherein said cam has a plurality of inclined areas interposed between gradual sloped areas that culminate in elevated areas.

17. The handle of claim 15 wherein said housing is T-shaped.

18. The handle of claim 15 which further includes two bearings, wherein in one of said bearings is on either side of said cam.

19. The handle of claim 15 wherein said bearings are ball bearings.

20. The handle of claim 15 wherein said slidable collar component has an exterior collar base.

\* \* \* \* \*